United States Patent
Marnfeldt

(10) Patent No.: US 9,119,964 B2
(45) Date of Patent: Sep. 1, 2015

(54) SYSTEM FOR DEEP BRAIN STIMULATION EMPLOYING A SENSOR FOR MONITORING PATIENT MOVEMENT AND PROVIDING CLOSED LOOP CONTROL

(71) Applicant: Boston Scientific Neuromodulation Corporation, Valencia, CA (US)

(72) Inventor: Goran N. Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/199,818

(22) Filed: Mar. 6, 2014

(65) Prior Publication Data

US 2014/0257427 A1   Sep. 11, 2014

Related U.S. Application Data

(60) Provisional application No. 61/773,476, filed on Mar. 6, 2013.

(51) Int. Cl.
*A61N 1/36* (2006.01)
*A61B 5/11* (2006.01)
*A61B 5/00* (2006.01)
*A61N 1/05* (2006.01)

(52) U.S. Cl.
CPC .......... *A61N 1/36067* (2013.01); *A61B 5/1101* (2013.01); *A61B 5/4836* (2013.01); *A61N 1/36139* (2013.01); *A61B 5/4082* (2013.01); *A61N 1/0534* (2013.01)

(58) Field of Classification Search
None
See application file for complete search history.

(56) References Cited

U.S. PATENT DOCUMENTS

| | | | |
|---|---|---|---|
| 5,716,377 A | 2/1998 | Rise et al. | |
| 6,094,598 A * | 7/2000 | Elsberry et al. | 607/116 |
| 6,227,203 B1 * | 5/2001 | Rise et al. | 128/898 |
| 7,151,961 B1 * | 12/2006 | Whitehurst et al. | 607/2 |
| 7,801,618 B2 | 9/2010 | Pless | |
| 7,974,696 B1 | 7/2011 | DiLorenzo | |
| 8,401,634 B2 | 3/2013 | Whitehurst et al. | |
| 8,554,325 B2 | 10/2013 | Molnar et al. | |
| 8,657,756 B2 * | 2/2014 | Stahmann et al. | 600/529 |

(Continued)

OTHER PUBLICATIONS

LeMoyne, Robert, Wearable and wireless accelerometer systems for monitoring Parkinson's disease patients —A perspective review Copyright ©2013 (R. LeMoyne/Advances In Parkinson's Disease 2 (2013)) pp. 113-115.

(Continued)

*Primary Examiner* — Brian T Gedeon
(74) *Attorney, Agent, or Firm* — Lewis & Reese, PLLC

(57) ABSTRACT

A closed loop system is disclosed for monitoring patient movements, such as tremors, and for automatically controlling an implantable stimulator device on the basis of the detected movements. The system includes a motion sensor such as a wearable item that contains an accelerometer to monitor a patient's movements, such as a ring locatable proximate to a patient's hand tremor. The motion sensor periodically transmits a feedback signal to the implantable stimulator device instructing it to change the stimulation parameters, such as current amplitude, in an attempt to reduce the tremor. The motion sensor can additionally communicate with other system components such as an external controller. In a preferred embodiment, the motion sensor and the implantable stimulator device communicate using short range electromagnetic radio waves.

24 Claims, 14 Drawing Sheets

(56) References Cited

U.S. PATENT DOCUMENTS

| | | | |
|---|---|---|---|
| 2008/0045775 A1 | 2/2008 | Lozano | |
| 2008/0058893 A1 | 3/2008 | Naujokat et al. | |
| 2008/0281381 A1 | 11/2008 | Gerber et al. | |
| 2009/0082641 A1* | 3/2009 | Giftakis et al. | 600/300 |
| 2009/0099627 A1* | 4/2009 | Molnar et al. | 607/62 |
| 2009/0264789 A1* | 10/2009 | Molnar et al. | 600/544 |
| 2011/0098780 A1* | 4/2011 | Graupe et al. | 607/45 |
| 2012/0016435 A1 | 1/2012 | Rom | |
| 2012/0158094 A1 | 6/2012 | Kramer et al. | |
| 2012/0197336 A1* | 8/2012 | Su | 607/41 |
| 2013/0123684 A1 | 5/2013 | Giuffrida et al. | |
| 2013/0184794 A1 | 7/2013 | Feldman et al. | |

OTHER PUBLICATIONS

Standaert, Jonas et al., "Implementing real-time step detection algorithm in EyesWeb enviromnment"; Master's Thesis in Electical Engineering, Jun. 2011; Blekinge Tekniska Högskola; Karlskrona, Sweden; KAHO Sint Lieven, Gent, Belgium.

Bakštein, Eduard; "Tremor Detection Algorithm for Parkinsonian Patients"; Diploma Thesis; Czech Technical University in Prague, Faculty of Electrical Engineering, Department of Cybernetics, Prague, 2010.

\* cited by examiner

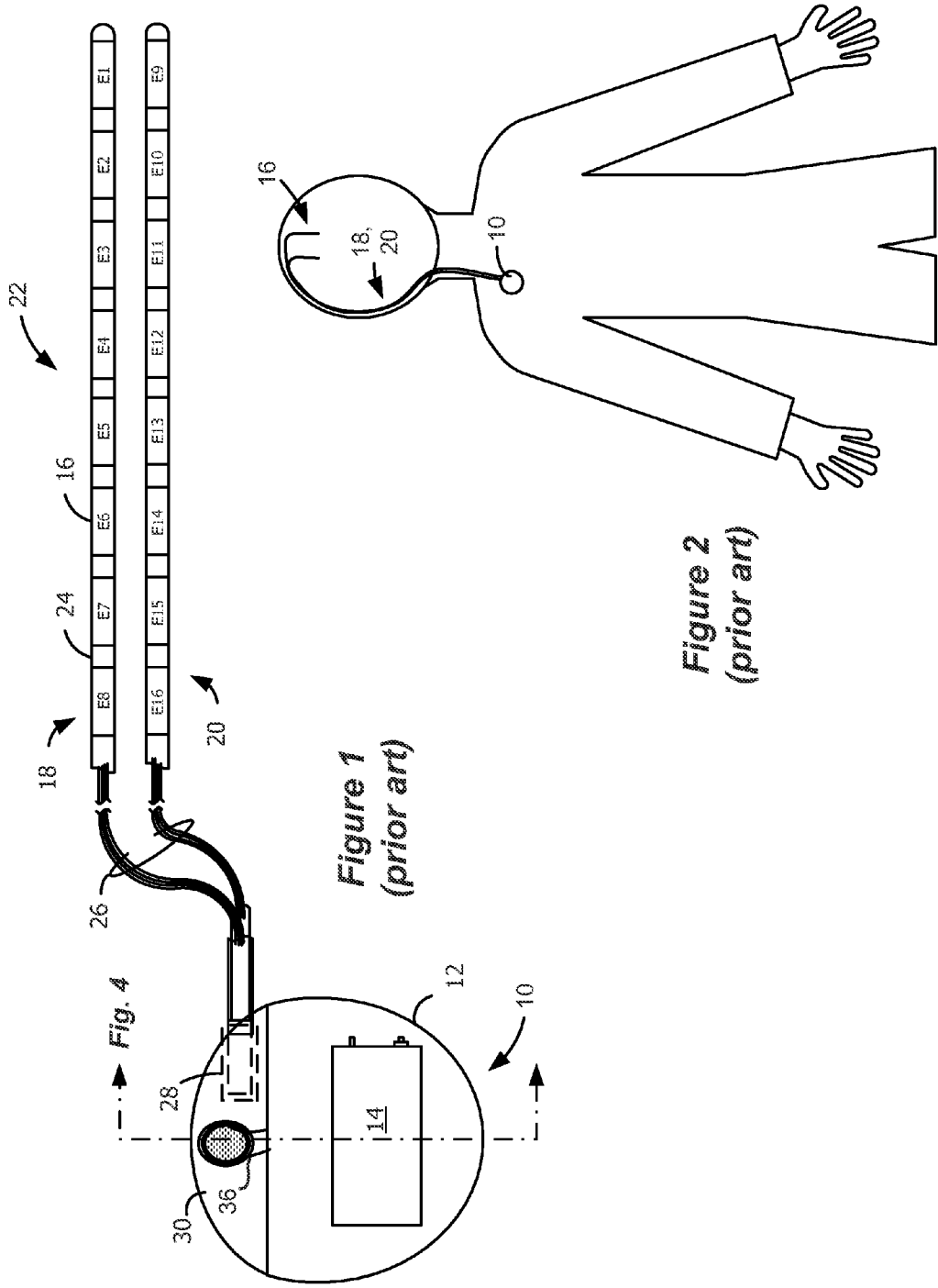

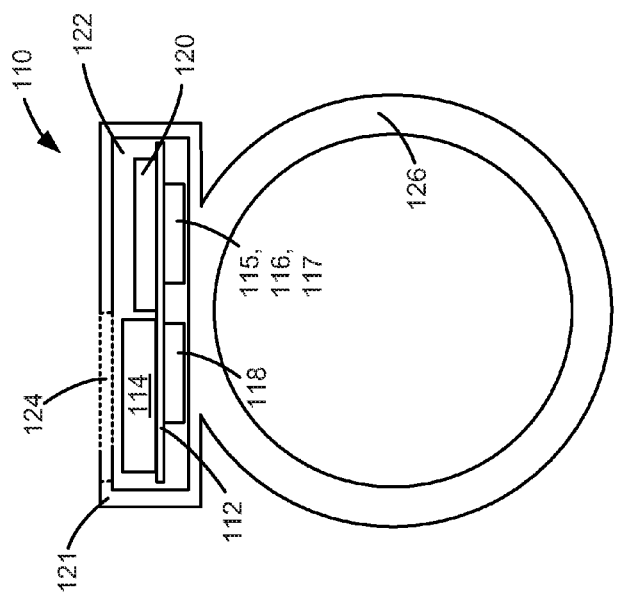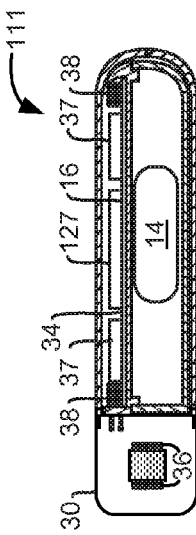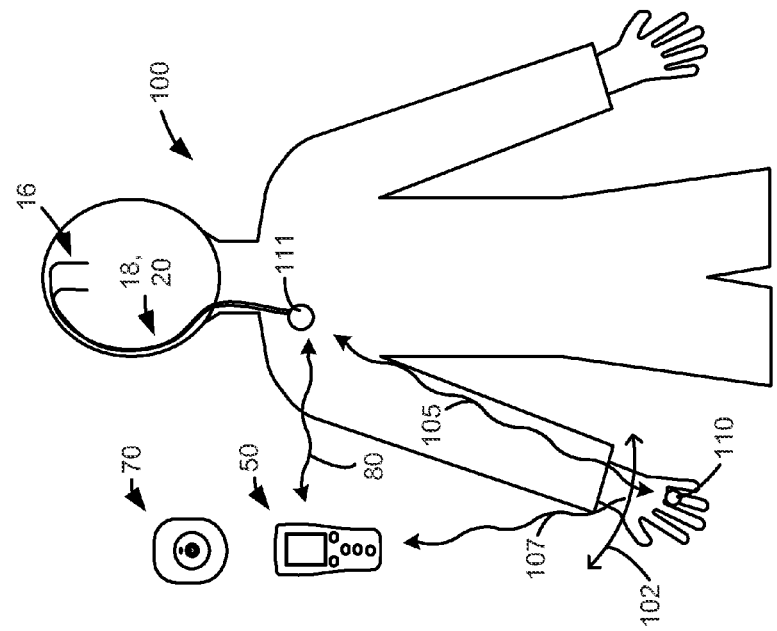

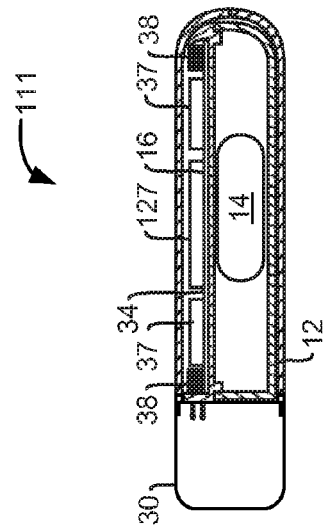
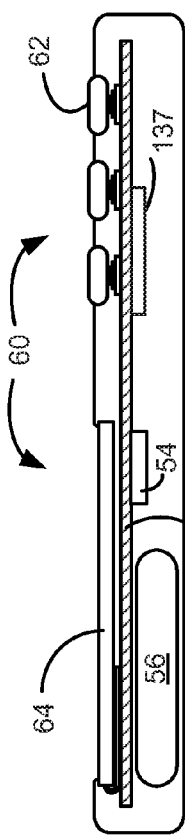
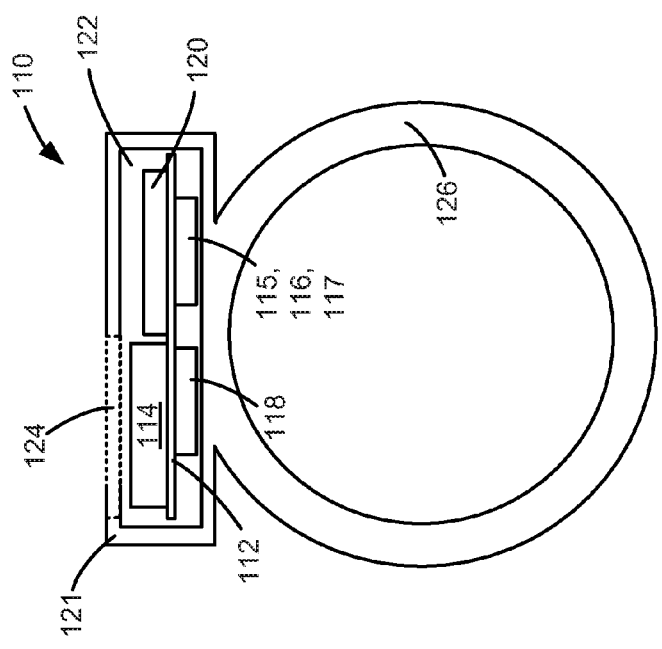

SYSTEM FOR DEEP BRAIN STIMULATION EMPLOYING A SENSOR FOR MONITORING PATIENT MOVEMENT AND PROVIDING CLOSED LOOP CONTROL

CROSS REFERENCE TO RELATED APPLICATIONS

This is a non-provisional patent application based on and claiming priority to U.S. Provisional Patent Application Ser. No. 61/773,476, filed Mar. 6, 2013, which is incorporated herein by reference.

FIELD OF THE INVENTION

The present invention relates to an improved implantable stimulator system including a motion sensor for monitoring patient movement and for communicating with the implantable stimulator to provide closed loop control based on such movement.

BACKGROUND

Implantable stimulation devices are devices that generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows will generally focus on the use of the invention within a Deep Brain Stimulation (DBS) system, such as is disclosed in U.S. patent application Ser. No. 13/741,116, filed Jan. 14, 2013. However, the present invention may find applicability in any implantable medical device system.

As shown in FIG. 1, a DBS system typically includes an Implantable Pulse Generator (IPG) 10, which includes a biocompatible device case 12 formed of titanium for example. The case 12 typically holds the circuitry and battery 14 necessary for the IPG to function, although IPGs can also be powered via external energy and without a battery. The IPG 10 is coupled to electrodes 16 via one or more electrode leads (two such leads 18 and 20 are shown), such that the electrodes 16 form an electrode array 22. The electrodes 16 are carried on a flexible body 24, which also houses the individual signal wires 26 coupled to each electrode. In the illustrated embodiment, there are eight electrodes on lead 18, labeled E1-E8, and eight electrodes on lead 20, labeled E9-E16, although the number of leads and electrodes is application specific and therefore can vary. The leads 18 and 20 couple to the IPG 10 using lead connectors 28, which are fixed in a header material 30 comprising an epoxy for example.

In a DBS application, as is useful in the treatment of Parkinson's disease for example, the IPG 10 is typically implanted under the patient's clavicle (collarbone), and the leads 18 and 20 are tunneled through the neck and between the skull and the scalp where the electrodes 16 are implanted through holes drilled in the skull in the left and right and side of the patient's brain, as shown in FIG. 2. Specifically, the electrodes 16 may be implanted in the subthalamic nucleus (STN) or the pedunculopontine nucleus (PPN). The electrodes may be implanted in both of these regions in the left and right side of the brain, meaning that four leads would be necessary, as shown in the above-referenced '116 application. Stimulation therapy provided by the IPG 10 has shown promise in reducing a patient's Parkinson's symptoms, in particular tremor that can occur in the patient's extremities.

As shown in cross section in FIG. 4, the IPG 10 typically includes an electronic substrate assembly including a printed circuit board (PCB) 34, to which various electronic components 37 are mounted; some of these components are discussed subsequently with respect to FIG. 5. Two coils (antennas) are generally present in the IPG 10: a telemetry coil 36 used to transmit/receive data to/from an external controller 50; and a charging coil 38 for charging or recharging the IPG's battery 14 using an external charger 70. The telemetry coil 36 can be mounted within the header 30 of the IPG 10 as shown, or can be located within the case 12, as shown in U.S. Patent Application Publication 2011/0112610.

FIG. 3 shows plan views of the external controller 50 and the external charger 70, and FIG. 4 shows these external devices in cross section and in relation to the IPG 10 with which they communicate. The external controller 50, such as a hand-held programmer or a clinician's programmer, is used to send data to and receive data from the IPG 10. For example, the external controller 50 can send programming data such as therapy settings to the IPG 10 to dictate the therapy the IPG 10 will provide to the patient. Also, the external controller 50 can act as a receiver of data from the IPG 10, such as various data reporting on the IPG's status. As shown in FIG. 4, the external controller 50, like the IPG 10, also contains a PCB 52 on which electronic components 54 are placed to control operation of the external controller 50; again some of these components are discussed with respect to FIG. 5. The external controller 50 is powered by a battery 56, but could also be powered by plugging it into a wall outlet for example. A telemetry coil 58 is also present in the external controller 50. A clinician's external controller is likely to only exist at a doctor's office, and not all patients having DBS implants will have patient external controllers. Alternatively, such patient external controllers may be limited in their functionality, such as merely allowing stimulation to be turned on or off.

The external controller 50 typically comprises a graphical user interface 60 similar to that used for a portable computer, cell phone, or other hand held electronic device. The graphical user interface 60 typically comprises touchable buttons 62 and a display 64, which allows the patient or clinician to operate the external controller 50 to send programs to the IPG 10 and to review any relevant status information that has been reported from the IPG 10 during its therapeutic operation.

Wireless data transfer between the IPG 10 and the external controller 50 typically takes place via magnetic inductive coupling. To implement inductive coupling functionality, both the IPG 10 and the external controller 50 have coils 36 and 58 respectively as already mentioned. Either coil can act as the transmitter or the receiver, thus allowing for two-way communication between the two devices.

Referring to FIG. 5, when data originating in the external controller's control circuitry 55 (e.g. a microcontroller) is to be sent from the external controller 50 to the IPG 10 along communication link 80, coil 58 is energized with alternating current (AC), which generates a magnetic field, which in turn induces a voltage in the IPG's telemetry coil 36. The generated magnetic field is typically modulated (51), such as by Frequency Shift Keying (FSK), which is well known in the art. The induced voltage in coil 36 can then be demodulated (11) at the IPG 10 back into the telemetered data signals, and fed to the control circuitry 15 in the IPG 10. This means of communicating by inductive coupling is transcutaneous, meaning it can occur through the patient's tissue 25.

If the communication involves adjustment to the therapy the IPG 10 is providing to the patient, the control circuitry 15 communicates relevant instructions to stimulation circuitry 27. As is known, stimulation circuitry 27 includes various current or voltage sources which can be coupled to selected electrodes 16 to provide desired therapy to the patient. Such therapy, typically referred to as a stimulation program, generally specifies various parameters for the stimulation, such as which electrodes 16 are active, whether such electrodes act as anodes (current sources) or cathodes (current sinks), and the duration, frequency, and amplitude of pulses formed at the electrodes. See, e.g., U.S. Patent Application Ser. No. 61/654,603, filed Jun. 1, 2012, for further details concerning stimulation circuitry 27.

To conserve power in the IPG 10, receiver circuitry the IPG 10 (e.g., demodulator 11) is typically only activated periodically during a short listening window to listen for communications from the external controller 50. For example, the demodulator 11 may be powered for only several milliseconds every second or so. The external controller 50 desiring to communicate with the IPG 10 will first broadcast a wake up signal recognizable by the IPG 10, which broadcast will typically continue for a long enough time to ensure that it overlaps at least one IPG listening window. Upon recognizing the wake up signal, the IPG 10 can fully power its communication circuitry, and transmit an acknowledgment signal back to the external controller 50 via modulator 13. The external controller 50 can in turn listen for this acknowledgment from the IPG 10 via its demodulator 53, which can occur after the external controller has finished broadcasting the wake up signal. Alternately, the wake up signal can contain gaps where its broadcast is temporarily suspended to listen for the acknowledgment signal. Once the acknowledgment is received and the IPG's communication circuitry fully powered, the external controller 50 can transmit its data to the IPG 10. Further details of this sort of handshaking between an external controller and an IPG can be found in U.S. Pat. No. 7,725,194, and U.S. patent application Ser. No. 13/211,741, filed Aug. 17, 2011. Typically, such communications between the external controller 50 and the IPG 10 will be predictably formatted in accordance with some protocol to ensure that communications are reliable. For example, communications may include header information, error checking data, an identification code of either or both of the transmitting and desired receiving device, etc.

The external charger 70 is used to charge (or recharge) the IPG's battery 14. Specifically, and similarly to the external controller 50, the external charger 70 contains a coil 72 which is energized via charging circuit 74 with a non-modulated AC current to create a magnetic charging field 84. This magnetic field induces a current in the charging coil 38 within the IPG 10, which current is rectified 17 to DC levels, and used to recharge the battery 14, perhaps via a charging and battery protection circuit 19 as shown. Again, inductive coupling of power in this manner occurs transcutaneously. The external charger 70 is generally held against the patient's skin or clothes and in good alignment with the IPG 10 by a belt or an adhesive patch, which allows the patient some mobility while charging. It should be noted that because of concerns of interference, the external controller 50 and external charger 70 will generally not operate at the same time, and instead one will take precedence over the other.

The IPG 10 can also communicate data back (86) to the external charger 50 using modulation circuitry 21 and switch 23, as described further in U.S. Patent Application Publication 2010/0305663. This form of communication is known as Load Shift Keying (LSK), and is useful to communicate data relevant during charging of the battery 14 in the IPG 10, such as the capacity of the battery, whether charging is complete and the external charger can cease, and other pertinent charging variables.

BRIEF DESCRIPTION OF THE DRAWINGS

FIG. 1 shows an implantable pulse generator (IPG) with an electrode array in accordance with the prior art.

FIG. 2 shows implantation of the IPG in a patient in a Deep Brain Stimulation (DBS) application in accordance with the prior art.

FIG. 6 shows a wearable motion sensor proximate to a location of tremor in a patient in accordance with the invention, and shows its ability to communicate with the IPG and/or the external controller.

FIG. 7A shows an example of the motion sensor in the form of a ring wearable on a patient's finger, in which the ring employ a MICS, MedRadio, or ISM frequency band antenna.

FIG. 7B shows an IPG modified to have a MICS, MedRadio, or ISM frequency band antenna to communicate with the ring.

FIGS. 10A-10D show an alternative embodiment of the system in which the ring, the IPG, and the external controller employ MICS, MedRadio, or ISM frequency band antennas.

DETAILED DESCRIPTION

The inventor realizes that DBS therapy as provided by the prior art system discussed in the Background suffers from the shortcoming of being an open loop control system for preventing tremor. During a fitting procedure, a DBS patient in conjunction with their clinician can attempt to determine a suitable stimulation program to relieve the patient's tremor symptoms. As mentioned earlier, such stimulation program can include which electrodes are active, whether such electrodes act as anodes or cathodes, and the duration, frequency, and amplitude of pulses formed at the electrodes. But such an initial stimulation program may not necessarily provide adequate treatment for the patient thereafter. As things change after fitting—e.g., as the electrodes 16 settle in the patient, or as the disease progresses, etc.—the initial stimulation program may no longer provide optimal therapy for the patient.

Figure 9B:
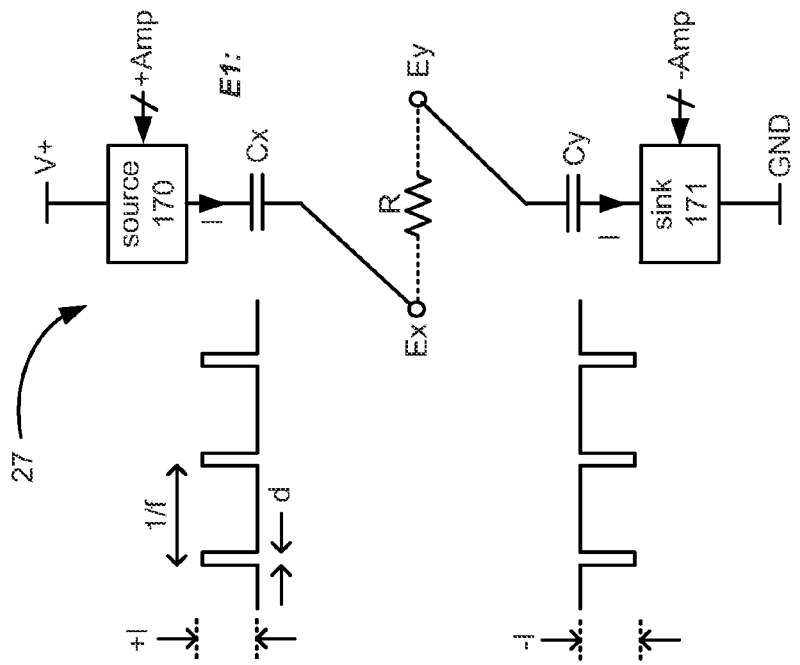
FIGS. 9A and 9B show use of the ring to control the therapy provided to the patient by the IPG.

The inventor understands the amplitude of the stimulation current provided to the patient to be an important parameter. FIG. 9B shows a simple example of part of the stimulation circuitry 27 in an IPG 10, and shows the provision of current pulses with an amplitude I through the patient's tissue, R, and between two selected electrodes Ex and Ey. The amplitude of I is set by current source 170 and current sink 171 via control signals (+Amp, −Amp) provided by the control circuitry 15. (Sources 170 and 171 can also comprise voltage sources for producing a constant voltage V between electrodes Ex and Ey to stimulate the tissue, although use of a constant current is discussed herein for simplicity). It can also be seen that the current pulses issue with a frequency f, and have a certain duration d. Presumably these aspects of the stimulation program were determined during fitting to provide tremor reduction for the patient. If for some reason the current amplitude I becomes too low, the patient's tremor may return. If I is too high—that is, if the current is more than is necessary to provide the patient relief from tremor—then power is needlessly wasted in the IPG 10. Moreover, if I is too high, the patient may suffer adverse effects. Therefore, it might be beneficial to reduce I, or to make other therapy changes, such as changes involving pulse frequency, duration, electrode choice, switching to a burst mode of stimulation, changing the pattern or shape of the pulse waveform, etc.

While the patient can use an external controller 50 (if he has one) to try and control his tremor, this may not always be practical. If the patient's tremors are significant enough, he may not be able to operate the user interface 60 of the external controller 50. Moreover, the external controller 50 is not helpful in certain situations, like when the patient is going to sleep. A patient can also lose or forget to carry the external controller 50. The external controller 50 can also simply be burdensome, particularly if the patient has to access it frequently.

Accordingly, the inventor feels that a closed loop control system would be beneficial—i.e., one in which patient response to therapy can be monitored and automatically used to control the therapy that the IPG provides to the patient.

As shown in FIG. 6, the patient is provided a motion sensor 110 that monitors the patient's movements and provides feedback to an IPG 111 so that therapy can be adjusted. In the example illustrated, the motion sensor comprises a wearable item such as a ring, which is proximate to and thus able to detect the patient's tremor 102. The ring 110 includes an accelerometer 118 for detecting the tremor 102, and communication circuitry for communicating feedback signals concerning tremor 102 to the IPG 111 via communication link 105. In some embodiments, the ring 110 can also communicate with the external controller 50 via communication link 107, as will be discussed subsequently.

System 100 allows the IPG 111 and the ring 110 to be placed in sensible, yet separate locations, with the ring near the tremor 102, and the IPG 111 near the tissue requiring stimulation. Because the locations of tremor and convenient IPG placement will not always be close to each other in the body, the disclosed technique improves upon prior art systems that incorporate accelerometers within the implants themselves. Even when such prior art implants incorporate accelerometers, they are not interested in determining the efficacy of the therapy provided by the implant. Moreover, such prior art implants would regardless not be suitable for the illustrated application, as the location of implantation does not match the location where relevant patient movement might occur.

A ring 110 capable of functioning as disclosed can be made in any number of ways, but one construction is shown in FIG. 7A. Ring 110 comprises a hoop 126 suitable to retain the ring on a patient's finger. The top side of the ring generally comprises a housing 121 containing a cavity 122. Inside the cavity 122 resides a printed circuit board 112, to which the accelerometer 118, a battery 114, control circuitry 115, a modulator 116, and a demodulator 117 are affixed. Also present is a short range electromagnetic radio wave antenna 120. A door 124 is provided to allow a user to gain access to remove or replace the battery 114. Although not shown, the ring 110 need not be powered by a primary disposable battery 114, but could instead be powered by a rechargeable battery. In such a case, the housing 121 of the ring 110 would include a port (e.g., a USB port; not shown) allowing for the recharging of the battery 114 in the ring. One skilled in the art will realize that the components of the ring 110 can be configured in the cavity 122 many different compact manners to reduce the ring's size.

Because the ring 110 must communicate with the IPG 111, the IPG 111 has been modified to also include a short range electromagnetic radio wave antenna 127, as shown in FIG. 7B. Note that the IPG 111 in this embodiment retains its telemetry coil 36 to allow it to continue to communicate with an external controller 50 via inductive coupling. However, the ring 110 can't communicate with the external controller 50 in system 100. Other examples of the system presented later allow for communication between the ring and the external controller, which provides certain advantages.

Short range electromagnetic radio wave antennas 120 and 127 can take many forms, but in a preferred embodiment comprises an antenna useable with the Medical Implant Communication Service (MICS) (402-406 MHz), MedRadio (401-457 MHz) or Industrial, Scientific and Medical (ISM) frequency bands. One skilled in the art will realize that any available ISM band can be used, taking their respective limitations into consideration, such as body attenuation at higher frequencies, or large antenna size at lower frequencies. Antennas 120 and 127 operable in these general frequency ranges (e.g., from about 400-450 MHz) are preferred for several reasons: (1) they are generally small enough for incorporation in the ring 110 and the IPG 111, (2) they provide energy at frequencies low enough to avoid over-attenuation in the patient's tissue, (3) they can communicate at suitably long distances (e.g., up to 10 meters), especially when compared to inductive coupling communication techniques such as illustrated in the Background, (4) are generally independent of alignment or orientation, again especially so when compared to inductive coupling communication techniques, and (5) frequencies in this band are generally allocated for medical use (although such use may be secondary to other limited primary uses) and thus are unlikely to interfere with non-medical devices. One example of an MISC short range electromagnetic radio wave antenna useable in both the ring 110 and the IPG 111 is Model No. ANT-403-SP, manufactured by Antenna Factor of Merlin, Oreg.

Figure 7C:
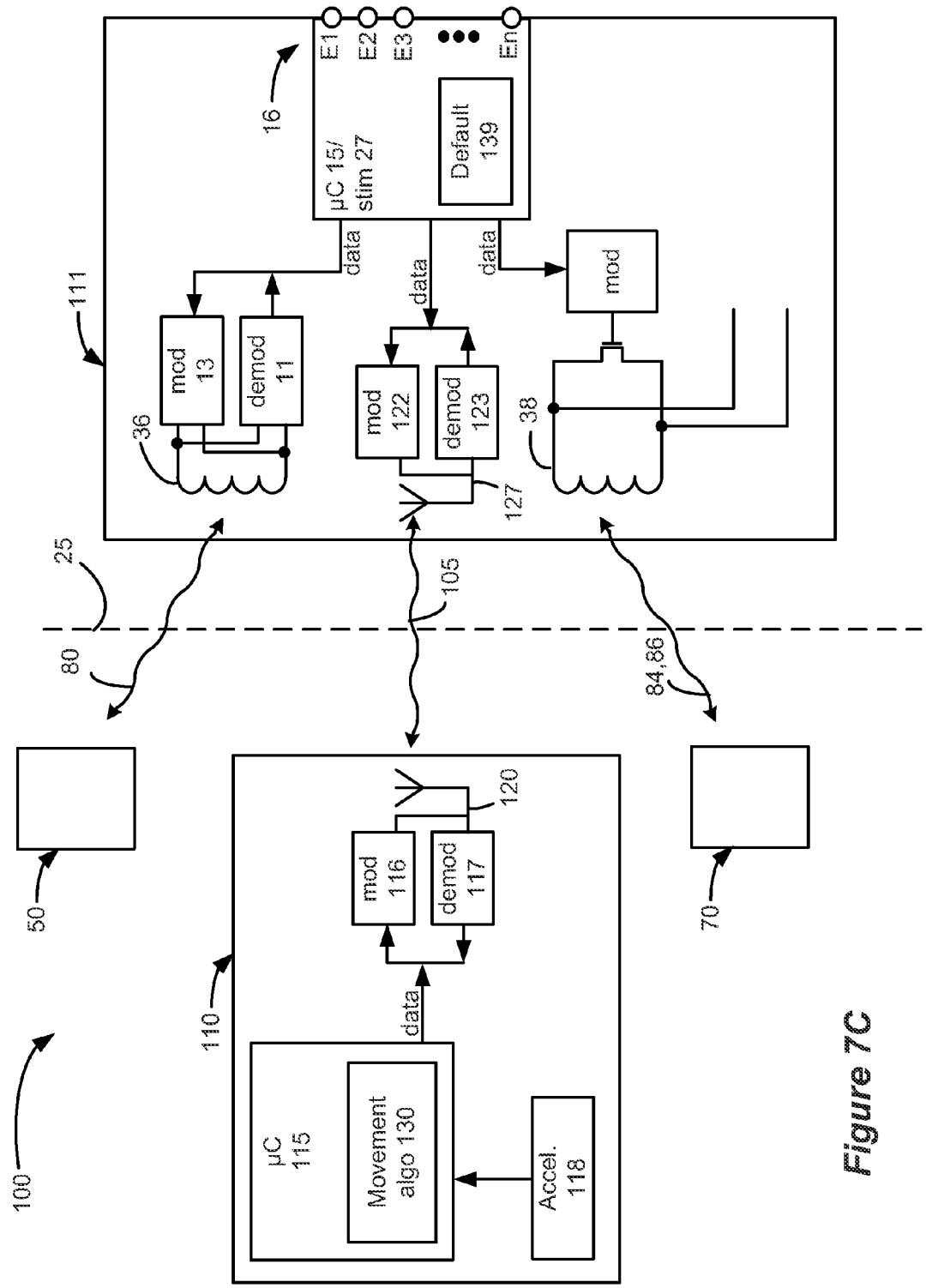
FIG. 7C shows the communication circuitry present in the ring and the IPG of FIGS. 7A and 7B, and the various communication paths in the system.

Circuitry for the system 100, including the ring 110, is shown in FIG. 7C. The ring's antenna 120 is coupled to modulation 116 and demodulation 117 circuitry operable at the above-mentioned frequencies and in accordance with a communication protocol selected for communications link 105. Likewise, the IPG's antenna 127 is coupled to complementary modulation 122 and demodulation 123 circuitry. This allows the ring 110 and the IPG 111 to bidirectionally communicate along communication link 105. Communications along link 105 can be established using a handshaking procedure, which may be dependent on the particular protocol chosen. Further, the ring 110 would be programmed with the IPG 111's ID code, and vice versa, to assist in such communications.

Modulation 13 and demodulation 11 circuitry, and coil 36 remain in the IPG 111 to maintain bi-directional inductive coupling communications with the external controller 50 along communication link 80, and thus the external controller 50 can remain unchanged in system 100. Charging of the IPG 111's battery can occur using external charger 70, which can also remain unchanged.

Figure 8:
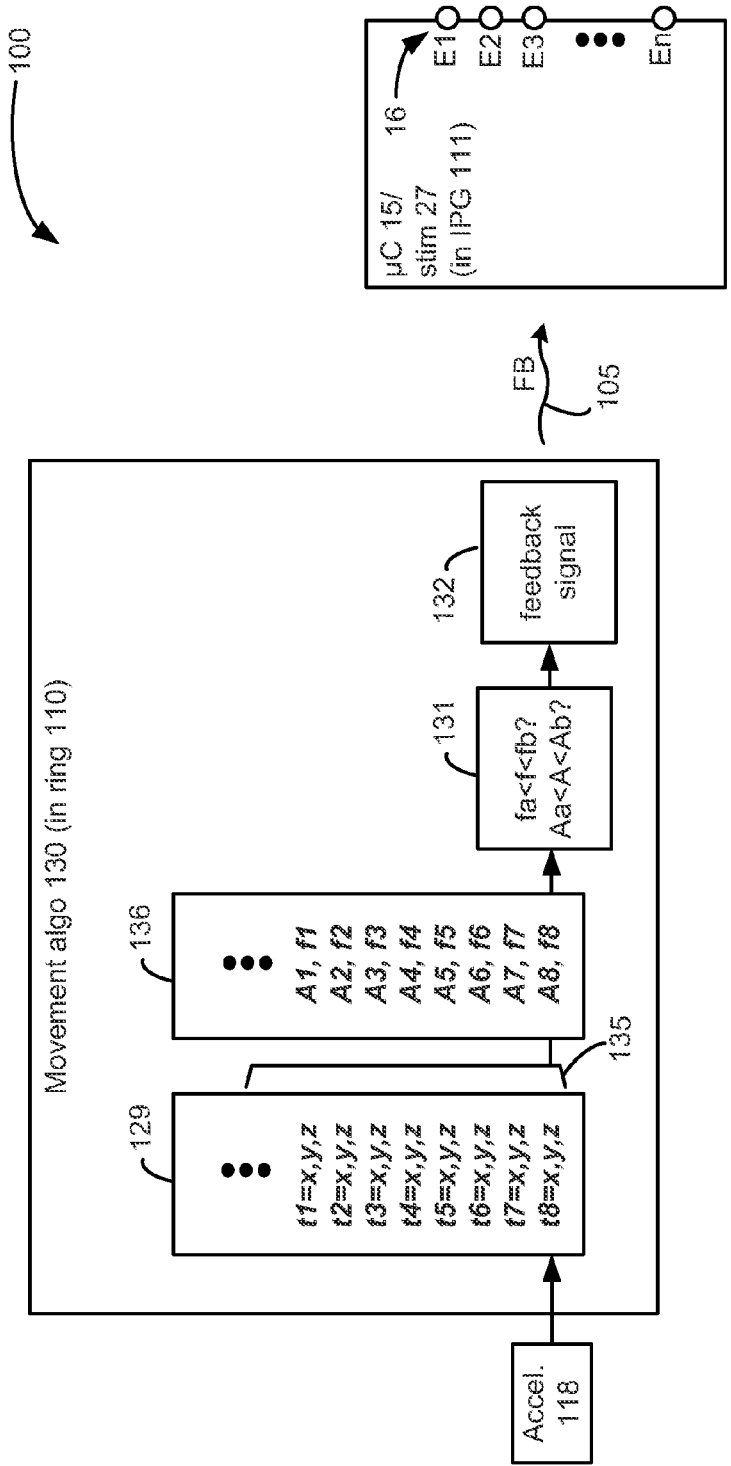
FIG. 8 show various manners by which the ring can communicate feedback signals to the IPG to adjust therapy.

Control circuitry 115 (e.g. a microcontroller) in the ring 110 can be programmed with a movement algorithm 130, which assesses data from the accelerometer 118 to determine when the patient is experiencing significant tremor 102. As shown in FIG. 8, the raw data from the accelerometer (forces detected in x, y, and z axes) are reported at a desired data rate and stored in a buffer 129. A periodic movement analysis module 136 uses a sliding time window 135 to consider only the raw data last reported over a certain time period and to determine tremor amplitude or tremor frequency over that time period. The time period encompassed by sliding time window 135 should be long enough to resolve several cycles of tremor—15 seconds for example. The module 136 analyzes the data in this time slice to determine whether there seems to be periodic movement, and if so, the amplitude (A) and frequency (f) of that movement. One skilled in the art will appreciate that module 136 may involve filtering to remove non-periodic signals, which may simply be a result of normal patient movement.

Module 136 may not be able to detect periodic movement over the time slice for two reasons. First, their simply might not be any movement (i.e., any tremor) because therapy is working, and hence module 136 would set A=0, and f=0 at that time. Second, the data may simply be too noisy (which could result from erratic but not tremor-based movement by the patient) for the module 136 to determine reliable values for A and f. In such a case, A=n/a, f=n/a, at least until this situation clears. In short, A and f are constantly updated by the module 136, to provide pseudo-real time analysis of the patient's movements.

The tremor amplitude A and tremor frequency f reported by module 136 are received by filter 131. Filter 131 can apply various thresholds to ignore data that would not logically correlate to patient tremor. For example, filter 131 can ignore frequencies f that are too high (above fb) or too low (below fa) to be indicative of patient tremor 102. Suppose that a given patient's tremor occurs at a frequency of 3 Hz. In this case, fa and fb may be set to 2 Hz and 5 Hz respectively. Filter 131 can also ignore amplitudes that are too high (above Aa) or too low (below Ab) to be indicative of patient tremor. One skilled in the art will understand that filter 131 may average or integrate the tremor amplitude and tremor frequency over a time period to arrive at stable values, although this isn't shown.

Thresholds fa, fb, Aa, and Ab can be programmed by the clinician upon observing a given patient's tremor, or can be set by the manufacturer. These thresholds can also be learned by the ring 110 by having the patient wear the ring during a period of tremor. During such training, the ring 110 can detect average frequencies and amplitudes for the tremor for that patient, and then can choose thresholds fa, fb, Aa and Ab spanning some reasonable range around those averages. Not all of these thresholds however are strictly necessary in a given implementation. Moreover, one skilled in the art will understand that the functionality of filter 131 can be built into module 136. However, they are shown separately here for clarity in understanding the analysis undertaken by movement algorithm 130.

Once filtered, the tremor values A and f are received by a feedback signal generator 132 which formats the data into a feedback signal (FB) to be transmitted to the IPG 111 to control or adjust the therapy provided by the stimulation circuitry 27. Feedback signal FB can comprise different pieces of information, such as: the tremor values A and f, or merely one of these values; an instruction to make a specific adjustment to the therapy, such as increasing or decreasing the current amplitude I either by set or variable amounts; or an entire stimulation program, specifying all stimulation parameters to be used by the stimulation circuitry 27. Once formed at the feedback signal generator 132, the feedback signal FB is then sent to the ring's modulator 116; broadcast from antenna 120 to antenna 127 in the IPG 111 via communication link 105; demodulated 11; interpreted by the IPG control circuitry 15; and passed to stimulation circuitry 27 for appropriate therapy adjustment. Transmission of the feedback signal is preferably preceded by necessary handshaking between the ring 110 and the IPG 111. Furthermore, the feedback signal will preferably be properly formatted at the signal generator 132 with an appropriate header, error encoding, and necessary ID codes. In essence, the ring 110 operates similarly to an external controller, albeit one that operates to adjust patient therapy automatically.

The feedback signals can be sent to the IPG 111 at logical times. For example, there may be little reason for the ring 110 to continuously send feedback signals to the IPG 111 in pseudo-real time if the ring doesn't detect significant changes—e.g., if tremor is under control, or if tremor is continuing. Instead, the ring 110 can transmit feedback signals when the ring detects a transition from a tremor-to-no tremor condition or vice versa. For example, if a continuing tremor has stopped, the feedback signal generator 132 sends a feedback signal to the IPG 111 to inform the IPG 111 that the current therapy settings are apparently working and that tremor is under control. If this no-tremor condition continues for an extended length of time, the ring 110 will not send further feedback signals as a power saving measure, subject perhaps to eventually sending a "beacon" feedback signal, as described below. If the ring 110 detects a transition from a no tremor-to-tremor condition, the feedback signal generator 132 sends a feedback signal to provide the IPG 111 the opportunity to try and alleviate the tremor in the various ways mentioned herein, such as by increasing the current amplitude I of situation. If the tremor continues, the feedback signal generator 132 may wait some period before sending another feedback signal—for example after 15 seconds. In other words, adjustment of therapy does not need to occur in pseudo-real time (although it can), and instead feedback signal can be sent at logical points in time to allow the IPG 11 time to take corrective action.

Even when tremor 102 appears to be under control, it may be reasonable for the feedback signal generator 132 to send a "beacon" feedback signal to the IPG 111 at longer time periods, for example, every five minutes or so. This allows the IPG 111 to understand that the ring 110 is still present and functioning, and that tremor is under control. If the ring 110 is not present (perhaps because it has been lost), or is not functioning properly (perhaps because its battery 114 is depleted), the IPG 111 can understand this when a beacon feedback signal has not been received at a proper interval (e.g., 5 minutes). At this point, the IPG 111 can change it mode of operation, realizing that it cannot (at least for the time being) rely on the ring 110 to provide it guidance as to how therapy should be adjusted. Thus, the IPG 111 can revert to default therapy settings 139, which may be stored in or associated with its control circuitry 15 (FIG. 7C). Default therapy settings 139 may comprise those determined during fitting to be generally helpful to the patient, and which are stored by a clinician's external controller 50; or, they may comprise therapy that over the course of operation of the system 100 has proven satisfactory for the patient. Once the ring 110 continues transmission of the beacon feedback signal or other feedback signals indicative of tremor (perhaps because the ring 110 has been found or its battery has been changed), the system 100 can work as described earlier. That is, use of default therapy settings 139 can be suspended, although such settings can continue to be updated as the ring 110 functions normally.

Figure 9A:
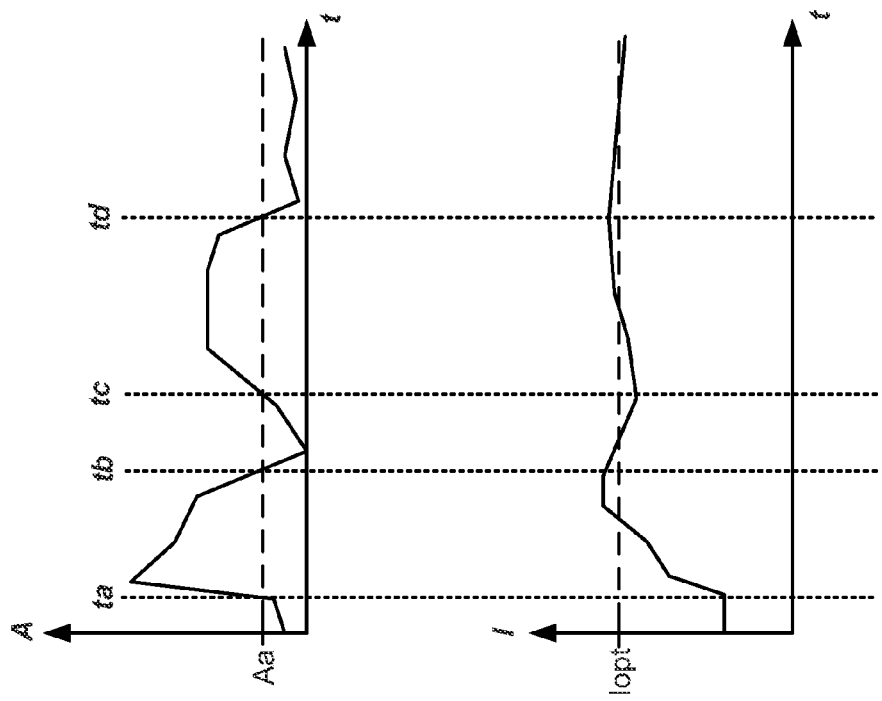

FIGS. 9A and 9B illustrate use of the ring 110 in modifying therapy for the patient. For simplicity, these figures illustrates modification of a single stimulation parameter—current amplitude I. One skilled should recognize that other stimulation parameters could also be modified, as explained elsewhere.

In this simple example, the existence of tremor 102 indicates that the current amplitude I should be increased, while the absence of tremor 102 may mean that the current amplitude can be decreased. In other words, even though the current amplitude I is currently effective to reduce tremor 102, it may be unnecessarily high. This can be wasteful of power in the IPG 111, and needlessly over-stimulate the patient, creating unwanted side effects. Accordingly, the current amplitude I is gradually reduced in this example by small amounts when no tremor is detected.

This is illustrated in FIG. 9A, which shows graphs of both tremor amplitude A and current amplitude I as a function of time. As seen at time ta, the patient's tremor amplitude becomes significant; for example, it is over threshold Aa described earlier. In response, the ring 110 instructs the IPG 111 by one or more feedback signals to increase the current amplitude I (or voltage as discussed earlier). This increase can occur in set amounts, or the amount of the increase can be set based on the tremor values. For example, if A is relatively large, the feedback signal may prescribe a larger increase in current amplitude, subject to a maximum amplitude set by the clinician or by the manufacture based on patient response or general considerations of safety. Thus, I rises from time ta to tb, and eventually at time tb, the patient's tremor amplitude has been reduced to an insignificant level (below Aa). Even though the tremor is insignificant at this point, the current amplitude I starts slowly decreasing from time tb to tc. At time tc, it is seen that the current amplitude I has decreased too far, because significant tremor amplitude A has returned. The ring 110 will sense this, and will again instruct the IPG 111 to increase the current amplitude I, as occurs from time tc to td, at which point the tremor amplitude is again brought under control. Starting at td, the current amplitude I again begin to slowly decrease, etc.

The effect of this closed loop control is that eventually the current amplitude I converges to an optimal value, Iopt, which controls the patient's tremor but not overly so. Moreover, this feedback from the ring 110 allows for adjustments to patient therapy that might be warranted from changes due to disease progression, or from settling of the IPG 111 and its electrodes after implantation.

Decreasing of the current amplitude I during periods of no tremor can occur in different ways. For example, the ring 110 can send a feedback signal instructing the IPG 111 to reduce the current slightly when no significant tremor has been detected. The beacon feedback signal discussed earlier may also suffice for this purpose.

In system 100, it should be noted that ring 110 can't communicate with the external controller (assuming one is present). This is unfortunate, because the ring 110 cannot benefit from the external controller's functionality, in particular its user interface 60.

Figure 5:
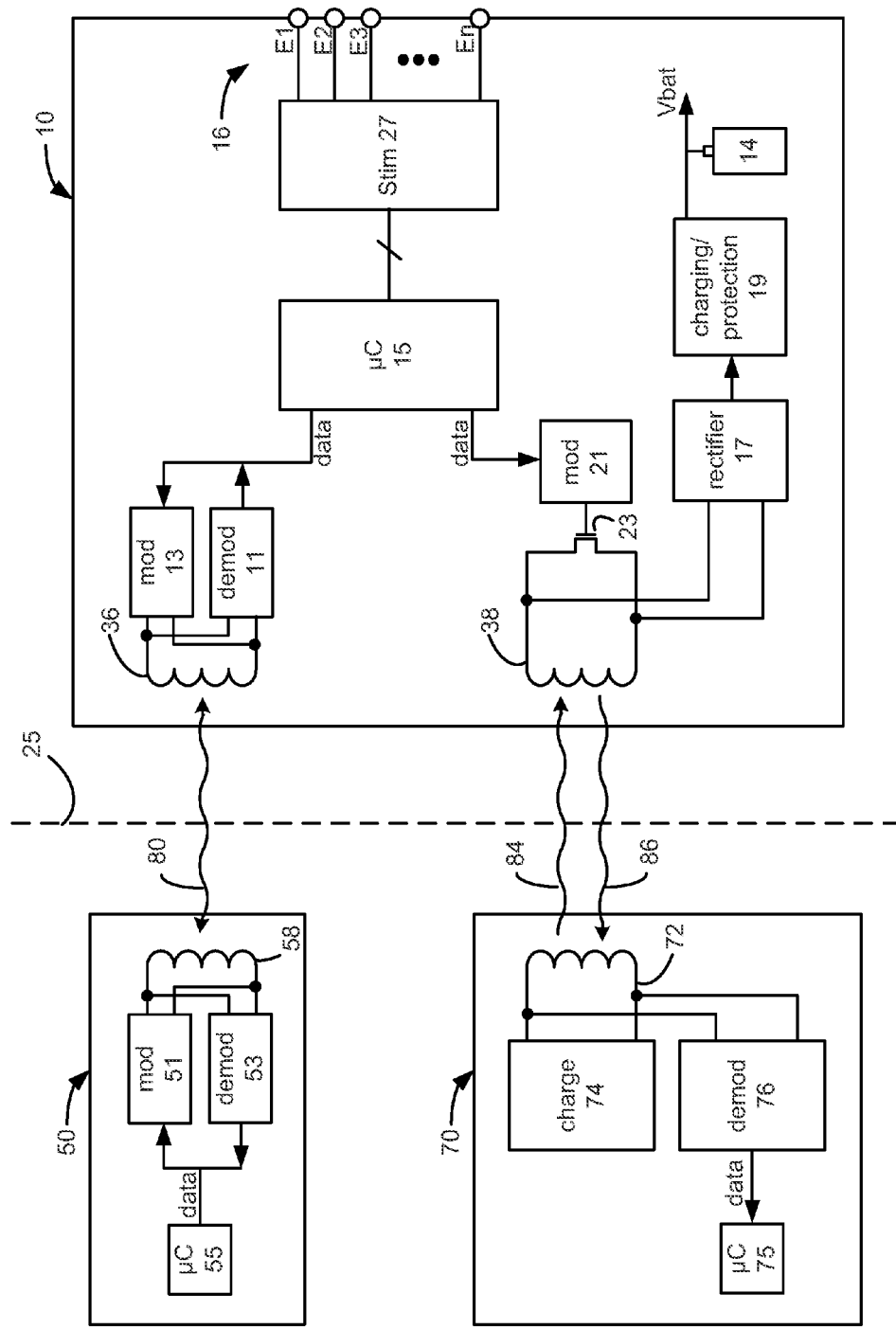
FIG. 5 shows the communication circuitry present in the external controller, the external charger, and the IPG in accordance with the prior art.
Figure 10D:
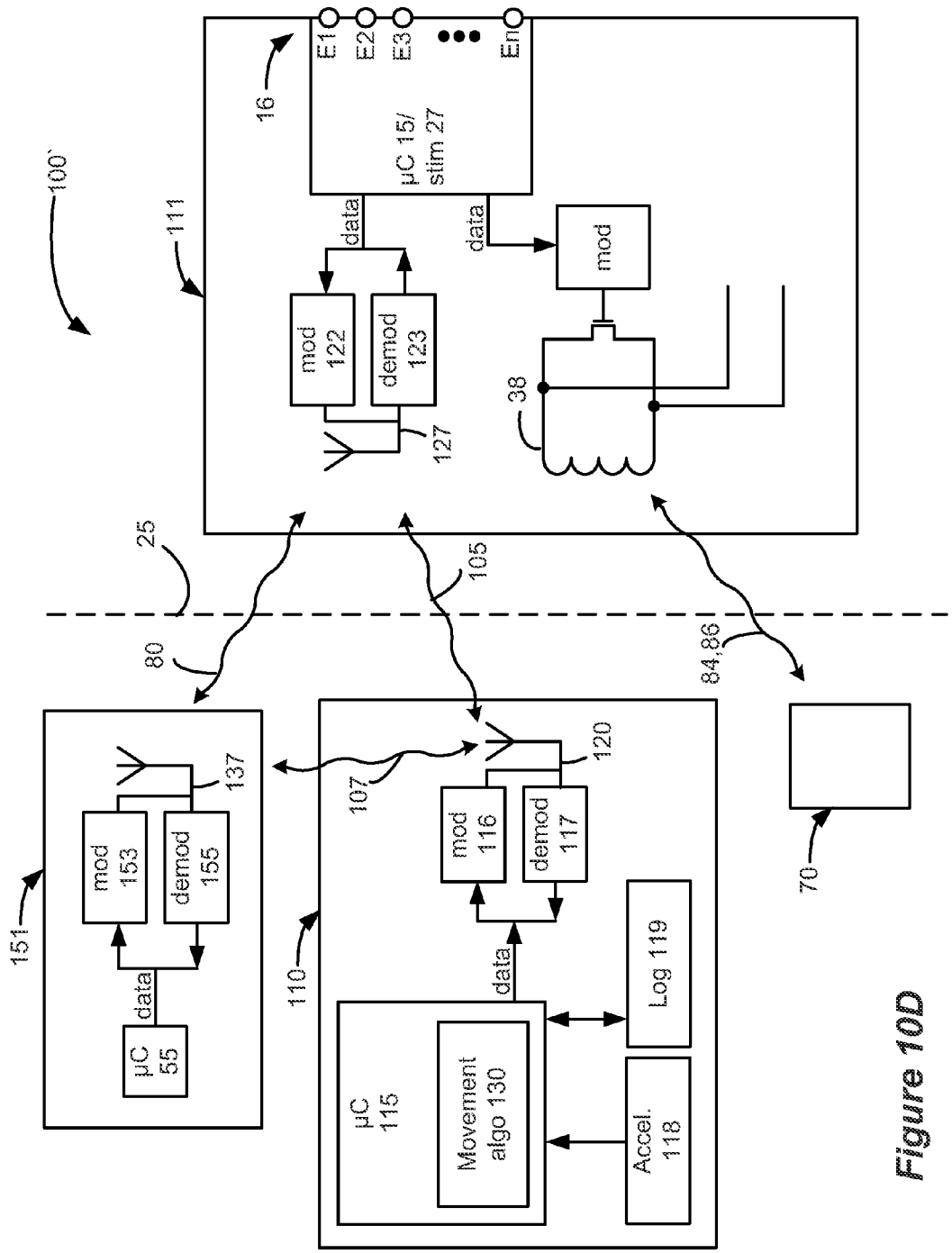

A modification to the system 100' that accomplishes connectivity with the external controller is shown in FIGS. 10A-10D. In this embodiment, the ring 110 and IPG 111 are as described earlier: each has a MICS, MedRadio, or ISM antenna 120 and 127 for communicating via link 105. In addition, the external controller 151 has been modified to contain a MICS, MedRadio, or ISM antenna 137, as shown in FIG. 10C, and compliant modulation 153 and demodulation 155 circuitry, as shown in FIG. 10D. This allows the external controller 151 to communicate with the ring 110 via link 107, and with the IPG 111 via link 80. Because short range electromagnetic radio wave communications are used in all aspects of the system 100' (except the charger 70), the external charger 151 and IPG 111 no longer require coil antennas (58, 36; FIG. 5) or associate modulation demodulation circuitry, and so these components have been removed (FIGS. 10B, 10C), which simplifies system 100' design. Additionally, this mitigates problems inherent in communications based on inductive coupling, such as short distances, and orientation or alignment concerns between devices. System 100' otherwise operates as described earlier to control patient tremor in a closed loop fashion, with the accelerometer 118 measuring patient tremor, and with the ring 110 sending feedback signals to the IPG 111 as necessary to adjust patient therapy.

Figure 11:
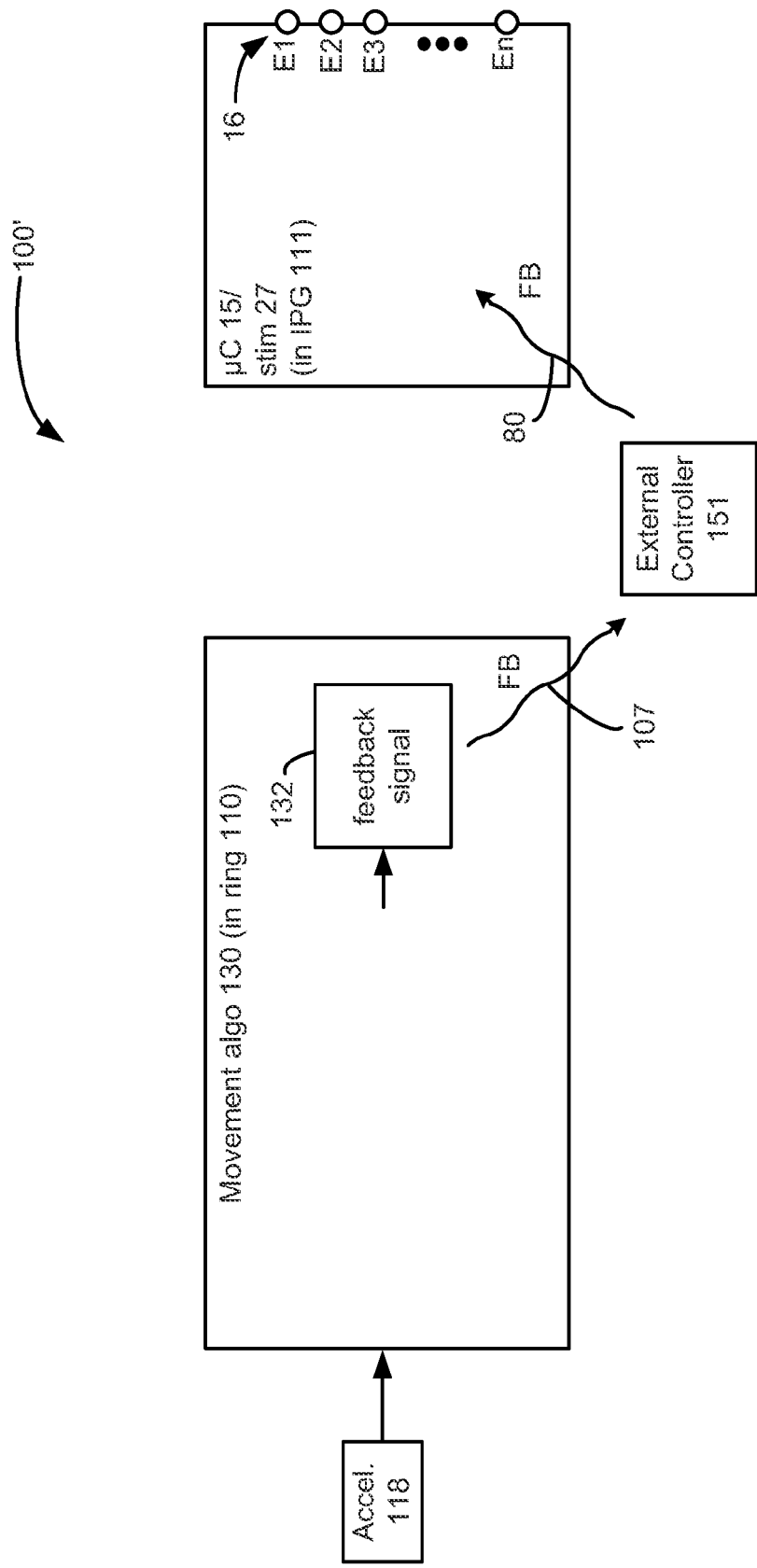
FIG. 11 shows various manners by which the ring and the external controller can communicate feedback signals to the IPG to adjust therapy.

Enabling communications between the ring 110 and the external controller 151 (if present) provides other benefits. For example, the external controller 151 can act as a communication hub between the ring 110 and the IPG 111, as shown in FIG. 11. Here, the feedback signals are sent to the external controller 151 via communication link 107. The external controller 151 in turn transmits the feedback signals to the IPG 111 via the communication link 80. The feedback signals transmitted on communication links 107 and 80 need not be exactly the same. Instead, the feedback data received from the ring 110 can be processed to some degree at the external controller 151. For example, the ring 110 can transmit the raw accelerometer data (x,y,z) to the external controller 151, leaving the external controller to analyze periodic movement in the data, to determine tremor amplitude A and frequency f, and to form an appropriate feedback signal to the IPG 111 based on that data, as described earlier with respect to FIG. 8. Distribution of data processing in this manner can take advantage of the improved processing capability of the external controller 50.

Figure 3:
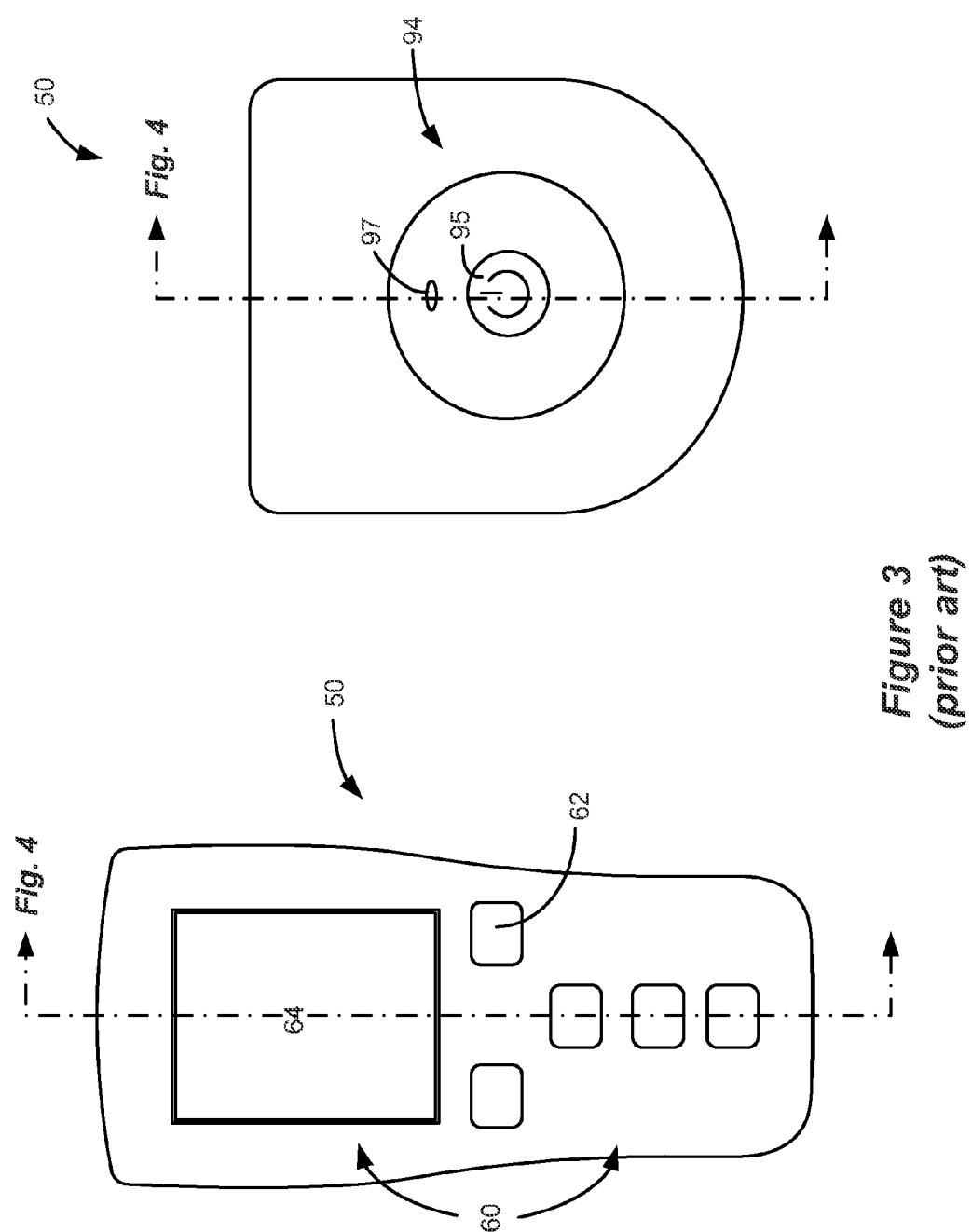
FIG. 3 shows plan views of an external controller and an external charger which communicate with the IPG in accordance with the prior art.

In addition to acting as a communication hub, communication between the ring 110 and the external controller 151 via link 107 can provide other system benefits. For example, the ring 110 can send status information to the external controller 151, such as the capacity of the ring's battery 114. The ring 110 can also store a log file 119 (FIG. 10D) indicative of communications with the IPG 111, which when transmitted to the external controller 151 can provide useful metrics to the patient or clinician regarding how well or how often the ring 110 is functioning to assist in adjusting patient therapy. Additionally, the external controller 151 can be used to control the ring 110. For example, the external controller 151 can be used to enable or disable operation of the ring 110. This is useful, for example, if a patient or clinician believes that closed loop control between the ring 110 and the IPG 111 is not operating properly, or is not needed at a particular time. Communications between the external controller 151 and the ring 110 further allows the ring to benefit from the flexibility provided by the external controller's user interface 60 (FIG. 3), and so the ring 110 can lack a user interface altogether, as user interface 60 can in effect comprise the user interface for the ring 110. However, this is not strictly necessary, and the ring 110 (or other wearable item) can comprise its own user interface.

Figure 4:
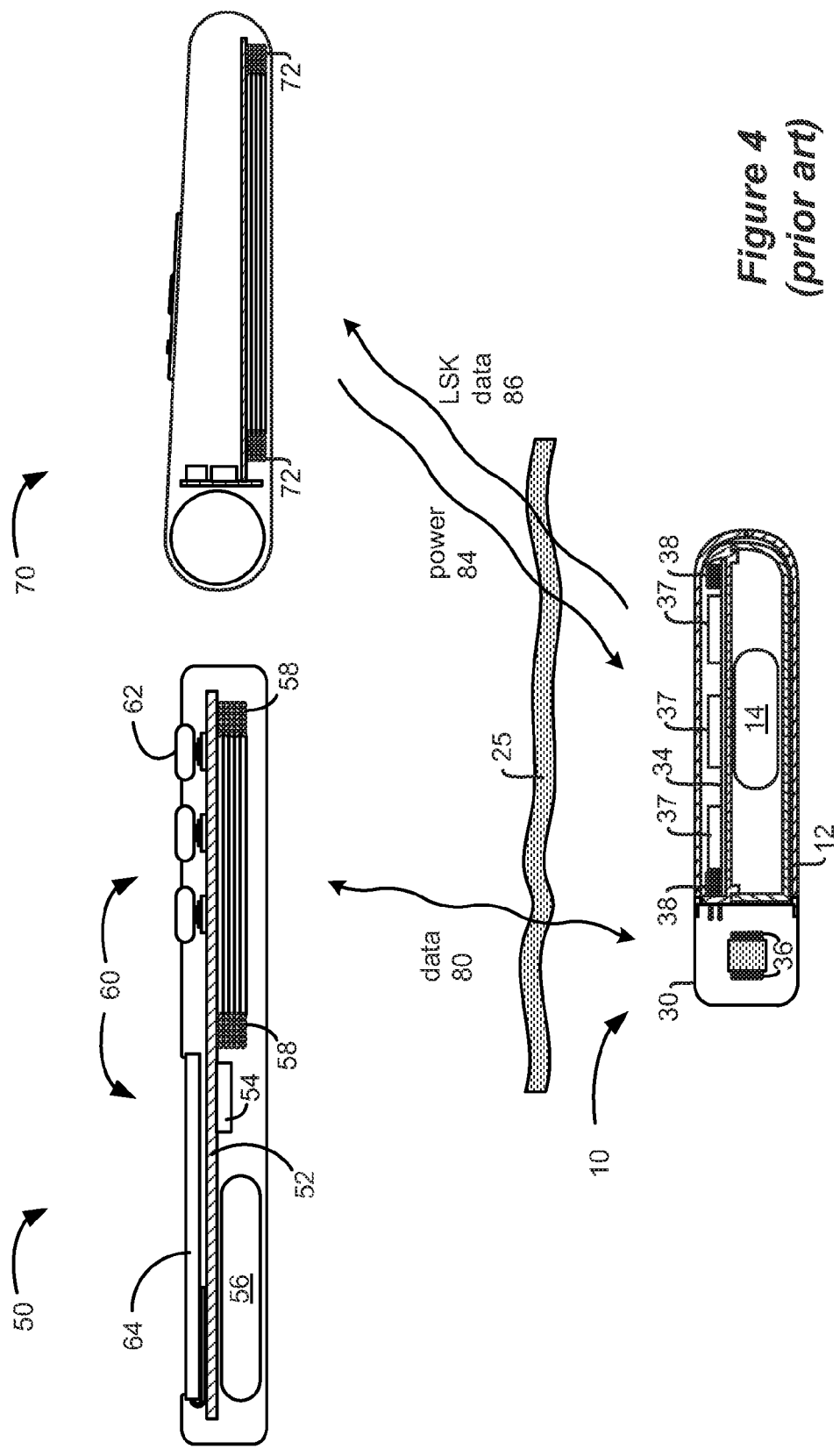
FIG. 4 shows cross sectional views of the external controller, the external charger and the IPG, and shows the communicative relations between these devices in accordance with the prior art.
Figure 12A:
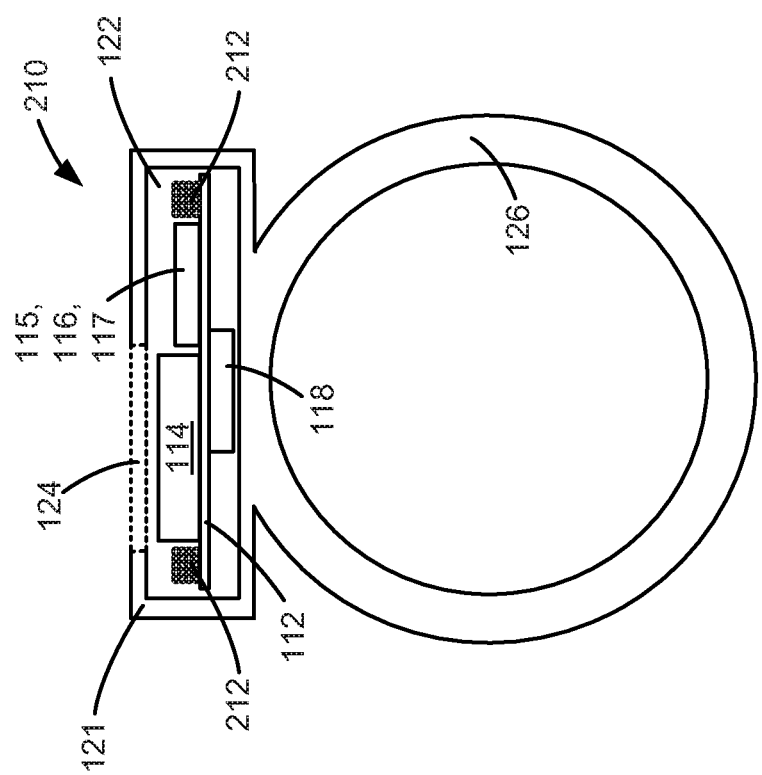
FIGS. 12A-12B show an alternative embodiment of the system in which the ring, the IPG, and the external controller all employ inductive coils for communications.
Figure 12B:
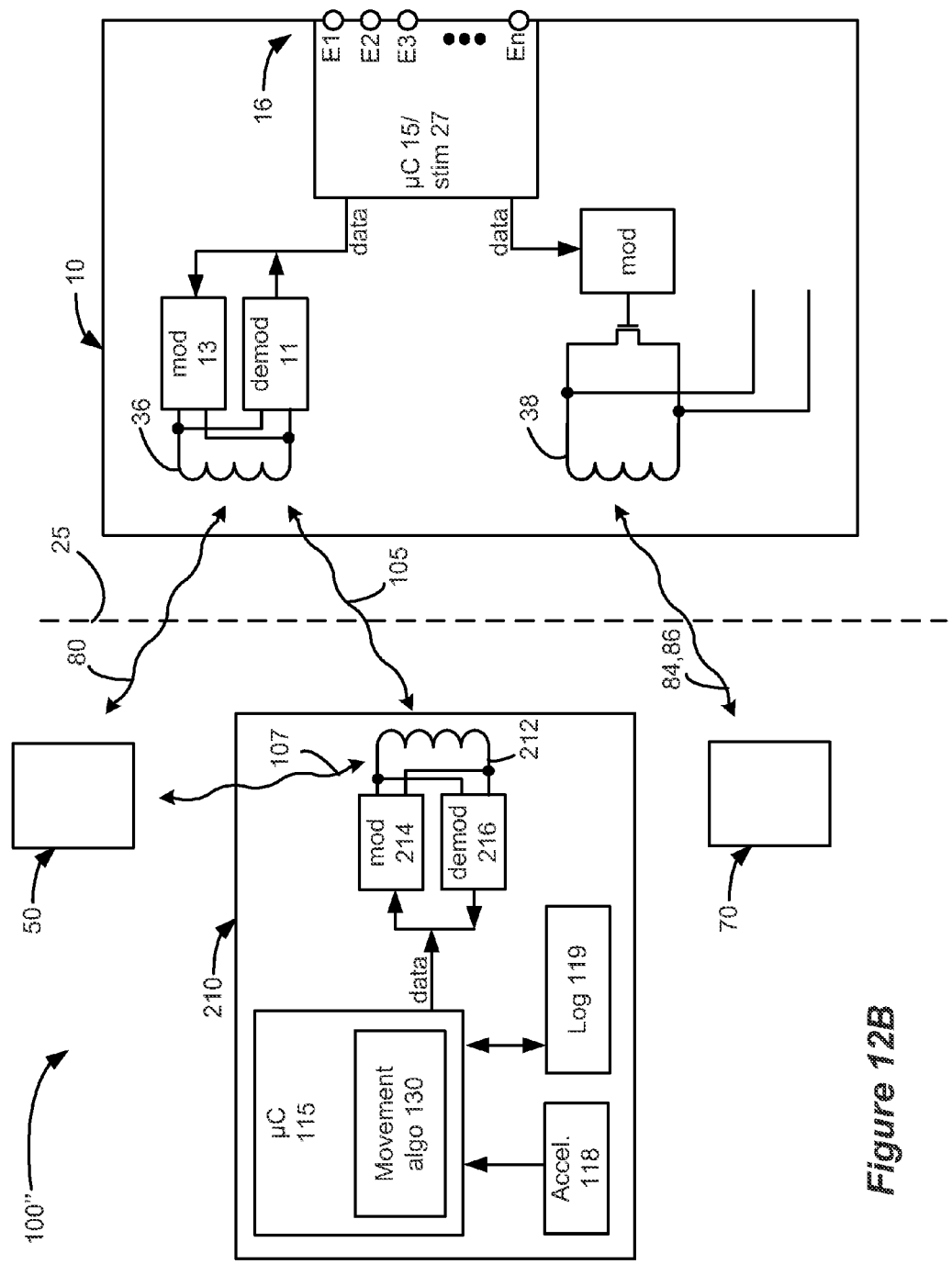

FIGS. 12A and 12B disclose another embodiment of a system 100" in which communications between the external controller 50, the IPG 10 and the ring 210 occur via inductive coupling. Thus, the external controller 50 and IPG 10 are as described earlier and contain telemetry coils 58 and 36 respectively (FIG. 4, 12B). So that the ring 210 can also communicate with these devices, it has been modified to include a telemetry coil 212, which is generally wound in a circular shape around the circumference of the ring's cavity 122 (FIG. 12A). Also present in the ring 210 are new modulation (214) and demodulation (216) circuitry designed to operate in accordance with legacy inductive coupling communications.

Thus, none of the devices in system 100" comprise short range electromagnetic radio wave antennas. This may make communications less reliable, particularly if the devices in system 100" are spaced at long distances with respect to each other or are poorly aligned. However, these shortcomings would not be problematic in all implementations of system 100". System 100" can otherwise operate as described earlier to control patient tremor in a closed loop fashion, with the accelerometer 118 measuring patient tremor, and with the ring 210 sending feedback signals to the IPG 10 or the external controller 50 to adjust patient therapy. Moreover, in system 100", the ring 210 can communicate with the external controller 50 with the same benefits noted earlier with respect to system 100'.

While use of MICS, MedRadio, or ISM frequency bands are preferable for the communication links in systems 100 and 100' which use short range electromagnetic radio wave communications, other means of electromagnetic radio wave communications can be used as well, including Zigbee™, Bluetooth™, WiFi, CDMA, TDMA, etc.

To this point, the feedback signal provided by the ring to the IPG has been disclosed for the purpose of adjusting the current amplitude I provided by the stimulation circuitry 27. However, other stimulation parameters—including which electrodes are active, whether such electrodes act as anodes or cathodes, the duration and frequency of the pulses, etc.—can also be adjusted by the feedback signal using the disclosed technique.

Figure 13:
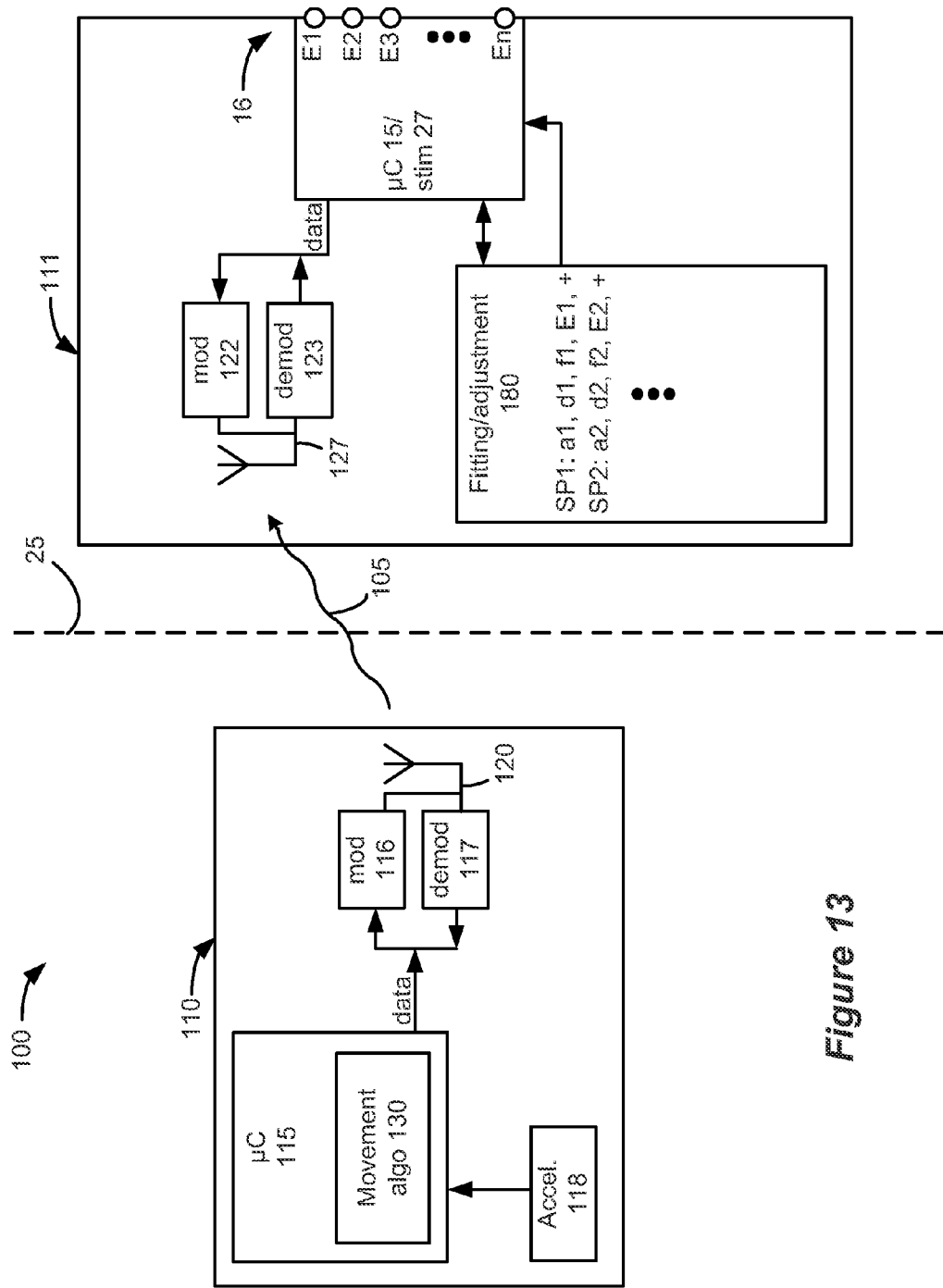
FIG. 13 shows a fitting/adjustment algorithm usable in the IPG in conjunction with feedback signals from the ring to adjust therapy.

In fact, the disclosed technique can assist with, or take the place of, a traditional fitting procedure during which an initial stimulation program is selected for a patient upon receipt of a new implant, as described earlier. For example, the IPG 111 can include a fitting/adjustment module 180, as shown in FIG. 13. (FIG. 13 shows implementation of fitting/adjustment module 180 in system 100, but the same could be implemented in systems 100' and 100" as well). When initiated—e.g., by the external controller, the ring, or otherwise—the fitting/adjustment module 180 can provide different stimulation parameters to the patient to gauge, in conjunction with the feedback from the ring, whether patient therapy (e.g., tremor) has improved.

For example, the fitting/adjustment module 180 can provide a first stimulation program (SP1) to the stimulation circuitry 27, prescribing the current amplitude (a1), pulse duration (d1), pulse frequency (f1), active electrodes (E1), and electrode polarity (+). Tremor 102 can then be monitored, and a feedback signal transmitted from the ring 110 to the IPG 111 in any of the manners mentioned earlier. The fitting/adjustment algorithm 180 upon receipt of this feedback signal can issue another simulation program (SP2) to see if it reduces tremor 102 even further by varying one of the parameters comprising the simulation program. If so, based on a subsequent feedback signal from the ring 110, the fitting/adjustment algorithm 180 can issue a new stimulation program (SP3) varying that parameter further in the hopes that that parameter will continue to show a positive effect on reducing tremor. If not, the fitting/adjustment algorithm 180 may select a new parameter to vary (SP3) to see if the variance of such new parameter improves tremor, based on a subsequent feedback from the ring 110, etc. In other words, the fitting adjustment algorithm 180 can proceed intelligently based on the received feedback signal from the ring 110 whether, or how to, modify the stimulation program being executed by the stimulation circuitry 27. Eventually, the fitting/adjustment algorithm 180 will be notified by the ring 110 that no further modifications are warranted, or the ring 110 will simply stop sending feedback signal transmissions, at which point the IPG 111 can deduce that the currently running simulation program is acceptable and is reducing patient tremor 102. Hence, through this intelligent search for an appropriate stimulation program, the IPG 111 will eventually settle on optimal stimulation program parameters that alleviate patient tremor.

While the motion sensor has been disclosed as a wearable item such as a ring, other motion sensors placeable proximate to patient tremor 102 can also be used, such as wrist bracelets, ankle bracelets, head bands, necklaces and the like. Motion sensors can also comprise adhesive patches that contain the relevant electronics and can be adhered to the patient's skin. Motion sensors can also be incorporated into a patient's clothing. For example, the motion sensor can be incorporated into the sleeve of a patient's shirt to monitor the patient's hand tremor, or can be adhered to the shirt using adhesive. Thus, hoops, bands, belts, necklaces, adhesives, and clothing all comprise means for retaining motion sensor proximate to the patient tremor.

Although not illustrated, a patient can also have more than one motion sensor that communicates with their IPG, for example, right and left rings, a ring and an ankle bracelet, etc. The use of more than one motion sensor would provide additional feedback regarding the effectiveness of patient therapy, and therefore may assist in tailoring treatment about the whole body, as opposed to merely one area of the body.

A motion sensor can also be an implantable device. For example, a motion sensor comprising the components discussed previously for the ring can be placed in a hermetic housing similar to the IPG, and implanted proximate to a source of patient tremor. Because such a motion sensor would not be externally accessible, it would logically have a rechargeable battery, similar to the IPG. An external charger 70 such as that described earlier could be used to charge the batteries in both the IPG and the implanted motion sensor.

While the disclosed technique is particularly useful in a DBS application, it can also be used to provide information about patient movement to other implantable stimulators, or to other medical implants more generally. This can be useful in the adjustment of the therapy provided by such devices.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system, comprising:
an implantable medical device configured to provide therapy to a patient experiencing patient tremor; and
at least one motion sensor, wherein the at least one motion sensor is configured to determine an amplitude and a frequency of patient movements and to transmit one or more feedback signals to the implantable medical device if the amplitude is between upper and lower amplitude thresholds and if the frequency is between upper and lower frequency thresholds,
wherein the implantable medical device is further configured to receive the one or more feedback signals and to adjust the therapy being provided to the patient based on the one or more feedback signals.

2. The system of claim 1, wherein the at least one motion sensor is configured to be wearable by the patient.

3. The system of claim 2, wherein the at least one motion sensor is configured to be affixable to the patient's skin by an adhesive patch.

4. The system of claim 2, wherein the at least one motion sensor comprises a means for retaining the motion sensor proximate to the patient tremor.

5. The system of claim 1, wherein the at least one motion sensor is implantable.

6. The system of claim 1, wherein the at least one motion sensor transmits the one or more feedback signals using short wave electromagnetic radio wave communications.

7. The system of claim 1, wherein the at least one motion sensor transmits the one or more feedback signals using inductive coupling.

8. The system of claim 1, wherein the at least one motion sensor comprises an accelerometer, and wherein the patient movements are sensed by the accelerometer.

9. The system of claim 1, wherein the one or more feedback signals comprise the amplitude and the frequency.

10. The system of claim 1, wherein the amplitude and the frequency are determined over a time period.

11. The system of claim 1, wherein the one or more feedback signals are transmitted and received periodically.

12. The system of claim 1, further comprising an external controller with a user interface configured to communicate with the implantable medical device.

13. The system of claim 12, wherein the at least one motion sensor and the external controller are configured to bidirectionally communicate with each other.

14. The system of claim 1, wherein the implantable medical device comprises a brain stimulator.

15. A device for monitoring patient tremor, comprising:
means for retaining the device proximate to a patient tremor;
a battery configured to provide power to the device;
an accelerometer configured to produce accelerometer data indicative of patient movements;
control circuitry comprising a movement algorithm, wherein the movement algorithm is configured to analyze the accelerometer data to determine an amplitude and a frequency of the patient movements;
transmission circuitry configured to form one or more signals if the amplitude is between upper and lower amplitude thresholds and if the frequency is between upper and lower frequency thresholds; and
an antenna configured to wirelessly transmit the one or more signals to an implantable medical device.

16. The device of claim 15, wherein the device comprises a ring, and wherein the means for retaining comprises a hoop.

17. The device of claim 15, wherein the means for retaining comprises an adhesive.

18. The device of claim 15, wherein the means for retaining comprises a band or belt.

19. The device of claim 15, wherein the means for retaining comprises an article of clothing.

20. The device of claim 15, wherein the antenna is configured to wirelessly transmit the one or more signals using short range electromagnetic radio wave communications.

21. The device of claim 15, wherein the antenna is configured to wirelessly transmit the one or more signals using inductive coupling.

22. The device of claim 15, wherein the one or more signals comprise the amplitude and the frequency.

23. The device of claim 15, further comprising a memory configured to store information regarding transmissions of the one or more feedback signals.

24. The device of claim 15, further comprising receiver circuitry configured to receive instructions from an external controller.

* * * * *